United States Patent
Carlisle et al.

(10) Patent No.: US 12,201,805 B2
(45) Date of Patent: Jan. 21, 2025

(54) SIMPLIFIED PNEUMATIC VOLUMETRIC PUMP USING IV DRIP CHAMBER

(71) Applicant: Pneuma Systems Corporation, Portsmouth, NH (US)

(72) Inventors: Jeffrey A. Carlisle, Stratham, NH (US); Brent Nibarger, Portsmouth, NH (US)

(73) Assignee: Pneuma Systems Corporation, Portsmouth, NH (US)

( * ) Notice: Subject to any disclaimer, the term of this patent is extended or adjusted under 35 U.S.C. 154(b) by 368 days.

(21) Appl. No.: 17/362,603

(22) Filed: Jun. 29, 2021

(65) Prior Publication Data

US 2021/0402082 A1   Dec. 30, 2021

Related U.S. Application Data

(60) Provisional application No. 63/045,259, filed on Jun. 29, 2020.

(51) Int. Cl.
   *A61M 5/14* (2006.01)
   *A61M 5/155* (2006.01)
   (Continued)

(52) U.S. Cl.
   CPC .......... *A61M 5/1411* (2013.01); *A61M 5/155* (2013.01); *A61M 5/16813* (2013.01);
   (Continued)

(58) Field of Classification Search
   CPC ................ A61M 5/1411; A61M 5/155; A61M 5/16854; A61M 39/24; A61M 2005/16863; A61M 2205/3379
   See application file for complete search history.

(56) References Cited

U.S. PATENT DOCUMENTS

| | | |
|---|---|---|
| 5,925,829 A | 7/1999 | Laragione et al. |
| 9,339,602 B2 | 5/2016 | Carlisle et al. |

(Continued)

FOREIGN PATENT DOCUMENTS

| | | |
|---|---|---|
| CN | 208726441 U | 4/2019 |
| CN | 211327440 U | 8/2020 |

(Continued)

OTHER PUBLICATIONS

European Patent Office, Supplementary Search Report for Application No. 1987218.2, dated Jun. 14, 2022, 8 pages.

(Continued)

*Primary Examiner* — Bradley J Osinski
(74) *Attorney, Agent, or Firm* — Nutter McClennen & Fish LLP

(57) ABSTRACT

A system includes a drip chamber. The drip chamber has a proximal end coupled with a drug container and a distal end coupled with fluidic tubing. The drip chamber has a proximal check valve configured to prevent fluid flow in a proximal direction and to allow fluid flow in a distal direction when a cracking pressure threshold is overcome. The drip chamber also includes a distal check valve configured to prevent fluid flow in the proximal direction and to allow fluid flow in the distal direction when a cracking pressure threshold is overcome. The cracking pressure threshold of the proximal check valve and the cracking pressure threshold of the distal check valve in combination is greater than or equal to 1 PSId. The system also includes a pneumatic port between the check valves that is configured to pneumatically couple with a pneumatic feedback control system.

10 Claims, 12 Drawing Sheets

(51) Int. Cl.
*A61M 5/168* (2006.01)
*A61M 39/24* (2006.01)
*A61M 39/28* (2006.01)

(52) U.S. Cl.
CPC .... *A61M 5/16854* (2013.01); *A61M 5/16881* (2013.01); *A61M 39/24* (2013.01); *A61M 2005/16863* (2013.01); *A61M 2039/242* (2013.01); *A61M 39/28* (2013.01); *A61M 2205/18* (2013.01); *A61M 2205/3344* (2013.01); *A61M 2205/3379* (2013.01); *A61M 2205/50* (2013.01)

(56) References Cited

U.S. PATENT DOCUMENTS

| | | |
|---|---|---|
| 10,173,003 B2 | 1/2019 | Davis |
| 10,342,920 B2 | 7/2019 | Carlisle et al. |
| 2003/0194328 A1 | 10/2003 | Bryant et al. |
| 2004/0073161 A1 | 4/2004 | Tachibana |
| 2004/0152944 A1 | 8/2004 | Medvedev et al. |
| 2009/0308484 A1 | 12/2009 | Nakagawa et al. |
| 2013/0102974 A1 | 4/2013 | Davis et al. |
| 2013/0153040 A1 | 6/2013 | Goto et al. |
| 2014/0091574 A1 | 4/2014 | Favy |
| 2014/0180084 A1 | 6/2014 | Vilks |
| 2014/0350511 A1* | 11/2014 | Carlisle ............... A61M 5/1452 604/126 |
| 2015/0094649 A1 | 4/2015 | Gittard |
| 2015/0322970 A1 | 11/2015 | Tanaka |
| 2016/0228637 A1 | 8/2016 | Carlisle et al. |
| 2018/0361040 A1 | 12/2018 | O'Toole et al. |
| 2020/0125124 A1 | 4/2020 | Carlisle et al. |
| 2022/0118178 A1 | 4/2022 | Carlisle et al. |

FOREIGN PATENT DOCUMENTS

| | | |
|---|---|---|
| EP | 1150105 A2 | 10/2001 |
| EP | 3069641 A1 | 9/2016 |
| JP | 5629277 B2 | 11/2014 |
| WO | 2014190188 A2 | 11/2014 |
| WO | 2020081846 A1 | 4/2020 |

OTHER PUBLICATIONS

[No Author Listed] Murata Manufacturing Co., Ltd.—"Microblower (Air Pump)", retrieved from the internet under <https://www.murata.com/en-us/products/mechatronics/fluid>, on Oct. 30, 2019, 4 pages.

International Search Report and Written Opinion for International Application No. PCT/US19/56783, mailed Jan. 6, 2020, 13 pages.

International Search Report and Written Opinion for International Application No. PCT/US21/39649 mailed Dec. 30, 2021, 23 pages.

[No Author Listed] Elvie Pump | Silent, Wearable, Smart Breast Pump, retrieved from the internet under <https://www.elvie.com/en-us/shop/elvie-pump> on Aug. 5, 2021, 12 pages.

International Search Report and Written Opinion for International Application No. PCT/US2021/055906, mailed Jan. 26, 2022, 9 pages.

International Preliminary Report on Patentability for International Application No. PCT/US2021/039649 mailed Jan. 12, 2023, 9 pages.

* cited by examiner

| Source of Error | Gravity Controlled | Illustrative Embodiments |
|---|---|---|
| 301 Changes in head height | Flow rate error | Automatic adjustment |
| 302 Pinched tube | Flow rate error | Kink resistant, small bore tubing |
| 303 Roller clamp drifts | Flow rate error | No roller clamp needed |
| 304 Changes in patient position | Flow rate error | Automatic adjustment |
| 305 Large diameter tubing | Waste of medication | Lower contained volume |
| 306 Changes in patient site backpressure | Flow rate error | Automatic adjustment |
| 307 Slide clamp not released | Failure to deliver | User alert |
| 308 Tube disconnection | Failure to deliver; Exsanguination | User alarm |
| 309 Bag inverts | Air ingress | Flow stops when inverted |
| 310 Drip calculation error | Flow rate error | No calc needed |
| 311 Delays in infusion start | Delay of therapy | User alert |
| 312 Failure to log therapy in medical record | Possibly duplication, loss of billing, incorrect fluid I/O calc | Automatic results reporting |

FIG. 10

SIMPLIFIED PNEUMATIC VOLUMETRIC PUMP USING IV DRIP CHAMBER

PRIORITY

This patent application claims priority from U.S. provisional patent application number 63/045,259, filed Jun. 29, 2020, entitled, SIMPLIFIED PNEUMATIC VOLUMETRIC PUMP USING IV DRIP CHAMBER, and naming Jeffrey Carlisle, Brent Nibarger, and Suzanne Barr as inventors, the disclosure of which is incorporated herein, in its entirety, by reference.

FIELD OF THE INVENTION

Various embodiments of the invention relate generally to precision delivery of fluids, and more particularly, various embodiments of the invention relate to IV drip chambers.

BACKGROUND OF THE INVENTION

A variety of known pumps are used for fluid dispensing in laboratory and medical settings. In the laboratory, pumps and pipettes are commonly used for both aspiration and dispensing of samples, reagents, chemicals, solutions, and other liquids. In medical applications, pumps are useful for providing medicaments to patients, especially for the delivery of medical therapies requiring an extended period of time and through various routes of delivery, including intravenously, intra-arterially, subcutaneously, intradermally, intraperitoneally, in close proximity to nerves, and into an intraoperative site, epidural space or subarachnoid space. In addition to medication delivery, pumps are also commonly found in hospital pharmacies drug compounding applications, especially with highly complex parenteral nutrition compounded solutions. In laboratory applications, fluid pumps are general purpose tools often in the form of syringe pushers or tube based peristaltic pumps.

SUMMARY OF VARIOUS EMBODIMENTS

In accordance with one embodiment of the invention, a system for delivery of a drug intravenously includes a drip chamber. The drip chamber has a proximal end configured to couple with a drug container and a distal end configured to couple with fluidic tubing that leads to a patient. The drip chamber has a proximal check valve configured to prevent fluid flow in a proximal direction. The proximal check valve is configured to allow fluid flow in a distal direction when a cracking pressure threshold of the proximal check valve is overcome. The drip chamber also includes a distal check valve configured to prevent fluid flow in the proximal direction. The distal check valve is further configured to allow fluid flow in the distal direction when a cracking pressure threshold of the distal check valve is overcome. The cracking pressure threshold of the proximal check valve and the cracking pressure threshold of the distal check valve in combination is greater than or equal to 1 PSId. The system also includes a pneumatic port configured to pneumatically couple with a pneumatic generator. The pneumatic port is positioned between the proximal check valve and the distal check valve.

In some embodiments, the combined cracking pressure of the two check valves is configured to withstand head pressure generated by a fully extended administration set. In some embodiments, the cracking pressure of each respective valve is greater than 1 PSId, 2 PSId, or 5 PSId. The cracking pressure may be less than about 10 PSId or 20 PSId.

The system may include, among other things, a spike at the proximal end configured to fluidly couple with a drug container. The spike may have a pneumatic port. The pneumatic port allows rigid drug containers to empty through the spike. The system may also include a reference volume with a precisely known invariant volume.

The system may also include a pneumatic generator configured to generate a positive pressure and/or a negative pressure in the drip chamber. A controller is configured to control the pneumatic generator. The controller may also communicate with and/or control pressure sensors, and fluidic switching valves. The pneumatic generator may generate pneumatic pressures with high precision on the order of 0.01 PSI or less, and/or less than 15% ripple in the pressure waveform. The pneumatic generator may be a tightly load coupled pneumatic driver, such as a piezoelectric microblower.

In some embodiments, at least one valve selectively causes the pressure generator to pump gas towards an atmospheric source or causes the pressure generator to pump gas towards the reference volume. A pneumatic valve may also selectively couple the drip chamber with the reference volume. A first pressure sensor may be coupled with the drip chamber and configured to determine the pressure in the drip chamber. A second pressure sensor may be coupled with the reference volume and configured to determine the pressure in the reference volume.

The controller and the pressure generator may be within a housing. The housing may include a drip chamber receiving portion configured to receive the drip chamber. The drip chamber may be physically and rotationally coupled with the housing.

In accordance with another embodiment, a method delivers a drug to a patient. The method provides a drip chamber. The drip chamber has a proximal end coupled with a drug container and a distal end coupled with fluidic tubing that leads to a patient. The drip chamber includes a proximal check configured to prevent fluid flow in a proximal direction. The proximal check valve is further configured to allow fluid flow in a distal direction when a cracking pressure threshold of the proximal check valve is overcome. The drip chamber also includes a distal check valve configured to prevent fluid flow in the proximal direction. The distal check valve is further configured to allow fluid flow in the distal direction when a cracking pressure threshold of the distal check valve is overcome. The method also provides a pneumatic port pneumatically coupled with a pneumatic generator. The pneumatic port is positioned between the proximal check valve and the distal check valve.

In some embodiments, the method generates a negative pressure within the drip chamber using the pneumatic generator. The negative pressure is sufficient to overcome the cracking pressure of the proximal check valve to move fluid from the drug container into the drip chamber. Additionally, or alternatively the method generates a positive pressure within the drip chamber using the pneumatic generator. The positive pressure is sufficient to overcome the cracking pressure of the distal check valve to move fluid from the drip chamber into the tubing that leads to the patient.

The method may also determine the volume of liquid in the drug container. The method continues to generate the negative pressure within the drip chamber until the volume of liquid in the drug container reaches a threshold. The negative pressure sufficient to overcome the cracking pressure of the proximal check valve is ceased when the volume of liquid reaches the threshold.

Among other things, the method may adjust the positive pressure within the chamber to achieve a given flow rate. The method may also identify that there is an occlusion in the tubing that leads to the patient. Accordingly, the method may vent the drip chamber and/or provide an alert.

The method may also determine the volume of liquid in the drug container. Positive pressure may be generated within the drip chamber until the volume of liquid in the drug container reaches a refill threshold. The positive pressure sufficient to overcome the cracking pressure of the distal check valve may be ceased when the volume of liquid reaches the refill threshold. In some embodiments, the method refills the drip chamber when the volume of liquid reaches the refill threshold by generating a negative pressure in the drip chamber.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 10 shows a table illustrating advantages of the above described illustrative embodiments as compared to common hazards for gravity based IV therapy.

DESCRIPTION

In illustrative embodiments, a fluid pathway delivers a fluid (e.g., containing a drug) to a patient in a precise and controlled manner. The fluid pathway includes a drip chamber coupled to a proximal check valve and a distal check valve, both of which allow fluid flow in a direction towards the patient (e.g., a distal direction). Each of the check valves has a relatively high cracking pressure (e.g., greater than or equal to 0.5 PSI). The drip chamber is pneumatically coupled with a controller having a tightly load coupled pneumatic driver and a reference volume. The controller uses the known pressure in the reference volume, the known volume in the reference volume, as well as the known pressure in the drip chamber to determine, among other things, a gas volume in the drip chamber. The determined gas volume provides feedback that controls the tightly load coupled pneumatic driver.

Various embodiments improve the safety and control of gravity intravenous infusions with a slight adaptation of a common tubing administration set and the application of precise pneumatic control of the pressure in a drip chamber, providing for the automatic monitoring, control, and reporting of results. One resultant benefit mitigates common hazards associated with IV gravity infusions without the undesirable cost and complexity of infusion pumps.

Figure 1:
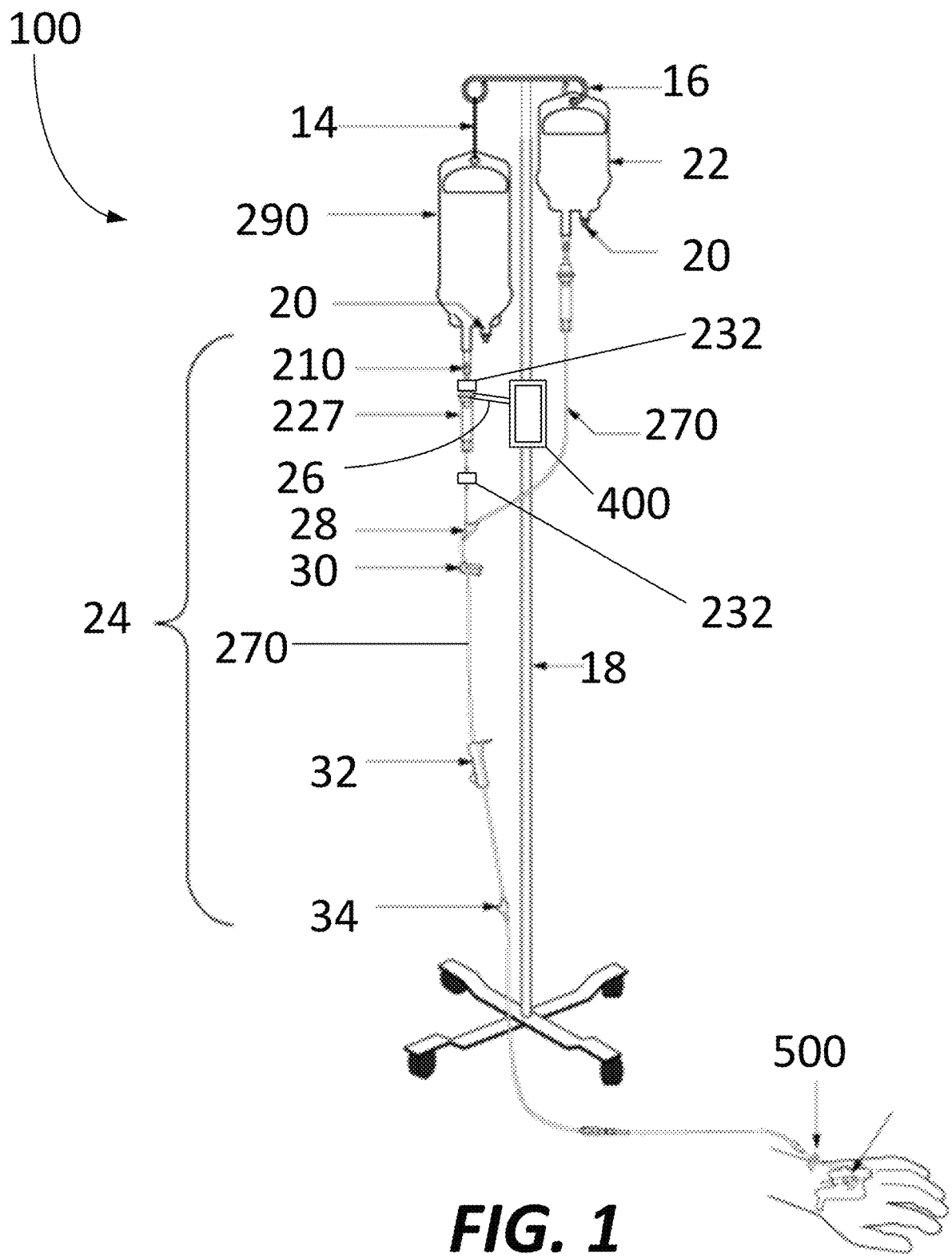
FIG. 1 schematically shows a system for fluid delivery in accordance with illustrative embodiments of the invention.

FIG. 1 schematically shows a fluidic system 100 for delivering a drug to a patient 500 in accordance with illustrative embodiments of the invention. The drug may be contained within a drug container 290, such as primary IV bag 290 hanging from an extender 14 coupled to a hook 16 on an IV pole 18. In some embodiments, the container 290 may have a liquid volume of, for example, 10 mL to 3,000 mL. The drug may be injected into the IV bag 290 via an injection port 20, prior to or while the IV bag 290 is fluidly coupled with the patient 500. In some embodiments, the system 100 may also include a secondary IV bag 22 also mounted on the IV pole 18. In a similar manner, the controller 400 may also be pneumatically coupled with the second drip chamber 227 (not shown), which is fluidly coupled with the secondary IV bag 22. Alternatively, or additionally, a second controller 400 may be pneumatically coupled with the second drip chamber 227. In illustrative embodiments the second drip chamber 227 may also include the proximal valve 232A and the distal valve 232B. Although FIG. 1 shows the system 100 with a secondary IV bag 22, various embodiments may operate with a single bag 290. Furthermore, although FIG. 1 shows the bag 290 hanging above the patient 500, illustrative embodiments enable the bag to be moved into a variety of positions, including below the patient's 500 heart.

The system includes an IV tubing set 24. The tubing set 24 includes a spike 210 configured to fluidly couple the IV tubing set 24 with the drug container 290. In practice, the spike 210 is positioned into a complementary opening in the IV bag or bottle 290. The tubing set 24 also includes a drip chamber 227. Typically, the drip chamber 227 is formed from a transparent plastic, such that the inside of the drip chamber 227 can be seen by medical staff. However, illustrative embodiments precisely control the volume inside the drip chamber 227, and therefore, the drip chamber 227 may be formed from opaque materials. As is known in the art, medical staff measure the speed of a manual IV setup by looking at the drip chamber 227 and counting the number of drops per minute. For example, if 25 drops are counted over the period of 60 seconds, the IV is infusing at a rate of 25 drops per minute, or 25 gtt/min. In reality, medical staff may not count the number of drops in a full minute; instead, they may count the number of drops, for example, over a period of 15 seconds, and then multiply that number by 4 to get the number of drops in a full minute.

Figure 2A:
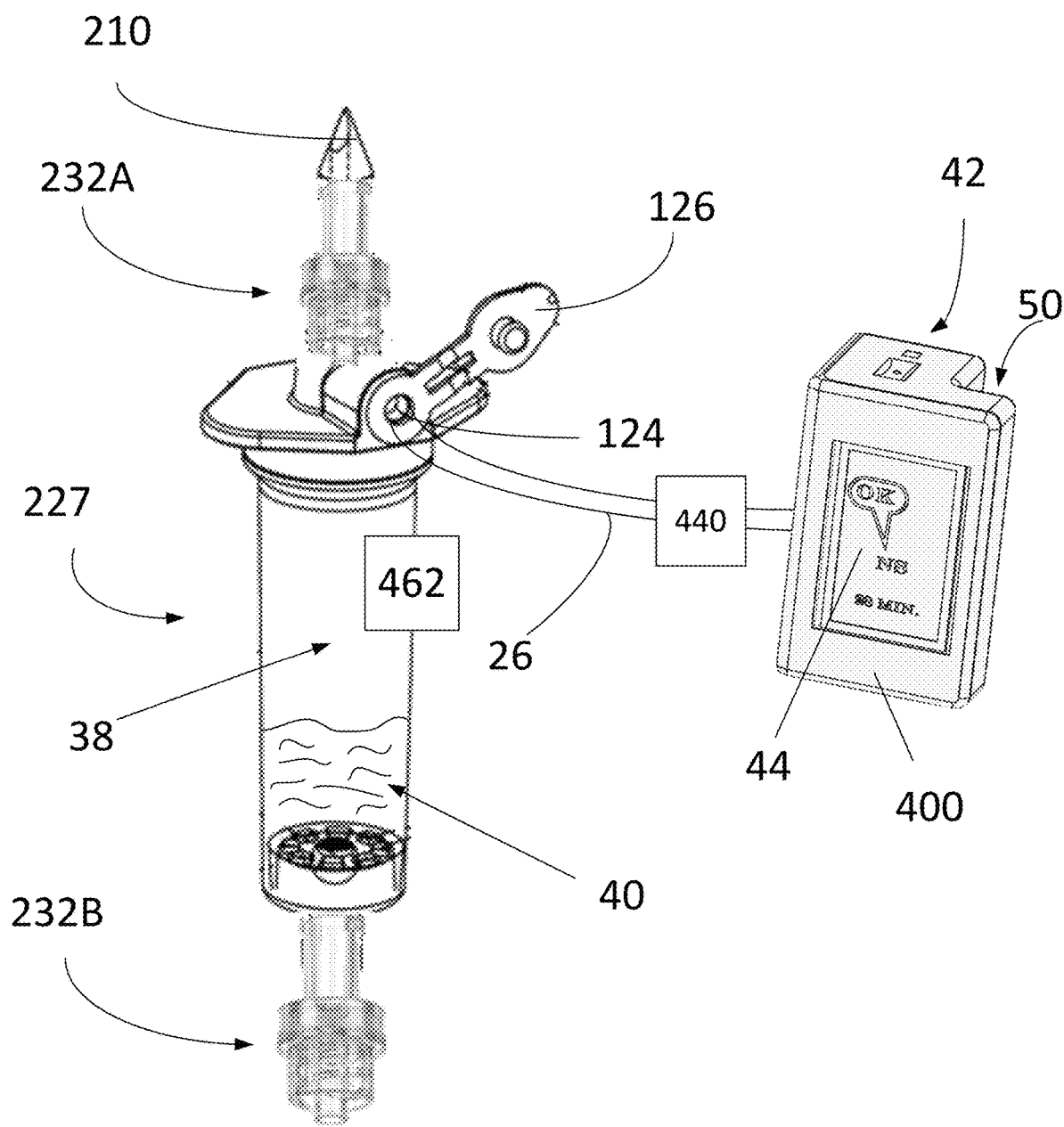
FIG. 2A schematically shows details of the drip chamber of the tubing set in accordance with illustrative embodiments of the invention.

FIG. 2A schematically shows details of the drip chamber of the tubing set in accordance with illustrative embodiments of the invention. Illustrative embodiments pneumatically couple the drip chamber 227 with the controller 400 that controls a pneumatic pressure generator (such as a tightly load coupled pneumatic driver). In FIG. 2A, the controller 400 is shown inside of housing 42. A medical practitioner may communicate with the controller 400 via a user interface 44 (e.g., touch screen interface 44). The user interface 44 allows users to select, among other things, a targeted flow rate, and also to set alarm conditions.

The pressure generator provides precise adjustment of the pressure and gas volume (and therefore the liquid volume) inside the drip chamber 227 (e.g., in accordance with user settings). As described further below, the controller 400 accurately calculates and controls the volume of gas inside the drip chamber 227 and also a flow rate from the drip chamber 227.

In the prior art, generally, the drip chamber 227 is kept about half-full. This is because if the drip chamber 227 is too full, medical practitioners are not able to see the drops to count them, and thus are unable to determine the rate at which the IV is infusing. On the other hand, if the drip chamber 227 is not full enough, then this allows air to get into the output IV tubing 270, which means that air would get into the patient's 500 circulatory system, which could be very dangerous, blocking a blood vessel or stopping the heart. In illustrative embodiments, the controller 400 precisely calculates the flow rate, and therefore, advantageously reduces or eliminates these risks. Furthermore, the controller 400 may detect the volume of any air bubble that makes it into output IV tubing 270.

The pressure generator pumps gas into the drip chamber 227 via a pneumatic coupling 26. To prevent and/or reduce the likelihood of fluid in the drip chamber 227 being pushed out of the drip chamber 227, the system 100 includes a proximal check valve 232A and a distal check valve 232B. Each of the check valves 232 has a relatively high cracking pressure beyond what is normally used with IV tubing. For example, each of the check valves 232 has a cracking pressure of 0.5 PSId or greater. In combination, the check valves 232A and 232B have a cracking pressure greater than 1.0 PSId.

Figure 2B:
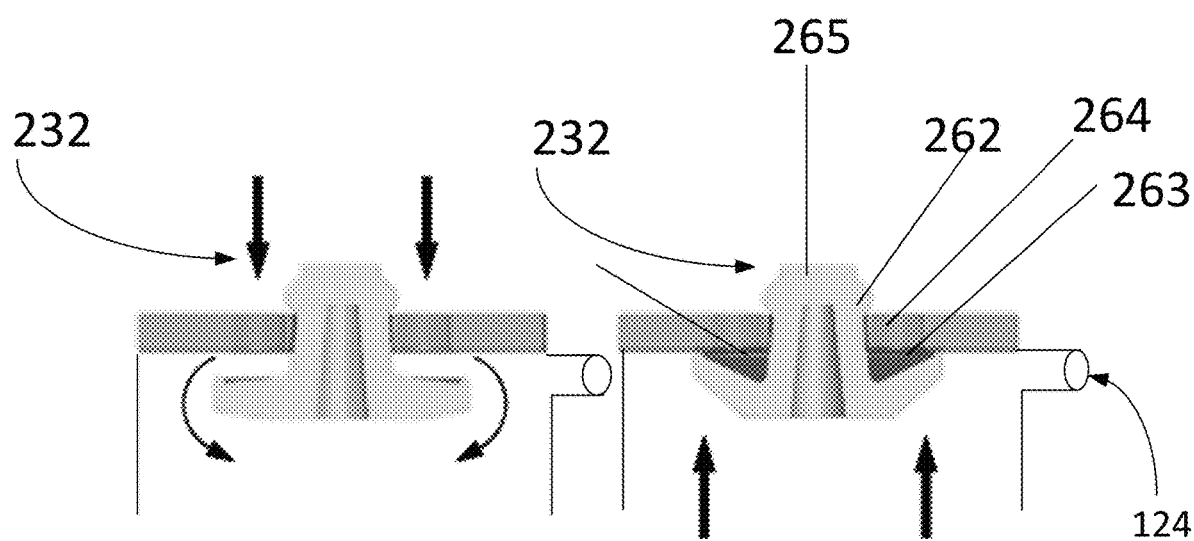
FIG. 2B schematically shows a check valve in accordance with illustrative embodiments of the invention.

FIG. 2B schematically shows a check valve 232 in accordance with illustrative embodiments of the invention. As shown, the check valves 232 may be passive valves. On the right side, back flow is prevented. However, on the left side, flow is supported after a cracking pressure threshold has been met. A flexible component 262 may fit into a rigid housing 264. The dimensions of the check valve 232 are controlled to provide reliable sealing of the fluid pathway that opens with a certain cracking pressure. Element 265 creates a tension that forms a liquid tight seal 263 of surfaces. There are a plurality of alternative forms to create such a check valve 232. In various embodiments, the check valve 232 may have a cracking pressure of equal to or greater than 1 PSId, 2 PSId, 3 PSId, or 5 PSId. Some embodiments may limit the cracking pressure to not greater than 10 PSId or 20 PSId.

In the prior art, it is known to use a check valve if a secondary infusion (e.g., from the secondary bag 22) is running. The check valves help to confirm that the fluid flows into the patient 500, rather than back up the primary line and into the fluid bag 290. A prior art check valve has low cracking pressure (e.g., to discourage backward flow from secondary IV bag 22 towards primary IV bag 290, but not to make it difficult for fluid to flow out of the drip chamber 227). In contrast, illustrative embodiments provide at least one proximal check valve 232A and at least one distal check valve 232B that each have a high cracking pressure (for both the proximal check valve 232A and the distal check valve 232B) so nothing flows into or out of the drip chamber 227 unless significant negative and/or positive pressure is applied by the controller 400. In some embodiments, the two check valves 232 have a total cracking pressure of at least 2 PSI. By using the proximal check valve 232A and the distal check valve 232B, a closed volume is generated therebetween that allows the controller 400 to receive pressure feedback and to provide precise control of the fluid flow into and out of the drip chamber 227.

Returning to FIG. 1, the system 100 may also include a distal injection port 28, where medicine or fluids other than those in the current IV bag 290 can be coupled/injected so that they infuse into the patient's 500 vein through the IV tubing 270. FIG. 1 shows four ports: the ports 20 on each of the primary IV bag 290 and the secondary IV bag 22, the port 28 below the drip chamber 227 that is connected with the secondary IV bag 22, and an injection port 34 close to where the needle goes into the patient's 500 vein. The injection port 20 on the actual IV bags 290, 22 may be used to mix medication with the fluid that is in the IV bag 290. Medication injected into this port 20 and mixed (e.g., by rolling the bag 290), causes the patient 500 to receive both the medication and the IV fluid at the same time. Some embodiments inject medication or a second kind of IV fluid directly so that it does not mix with the IV fluid bag 290 (e.g., into one of the ports 28 or 34 that are located below the drip chamber 227).

The system may also include a slider clamp 30 and/or a roller clamp 32. The roller clamp 32 controls the rate at which the IV fluid infuses. IV medication is ordered to infuse at a specific rate, and one of the major tasks of hospital nurses is to set up the IV so that it infuses at the prescribed rate and to adjust the IV periodically if the rate has changed so that it remains at the ordered rate. The rate at which an IV fluid infuses is referred to as the IV infusion rate or flow rate. Illustrative embodiments deliver a targeted flow rate by using pressure feedback (directly or indirectly) from the drip chamber 227.

As known by those of skill in the art, rolling the roller clamp 32 one way squeezes the IV tubing 270 more tightly, making it more narrow and therefore making the fluid flow through the tubing slower. If the roller is rolled the other way, it loosens its pinching of the IV tubing 270, making the tubing less narrow, and allowing the IV fluid to flow through at a faster rate. For example, if the medical practitioner determines (by looking at the drip chamber and counting drops) that an IV is infusing at a rate of 50 gtt/min, but it was ordered to infuse at a rate of 30 gtt/min, the roller clamp 32 may be tightened to slow the drip rate down until only 30 drops are counted going through the drip chamber 227 each minute.

Illustrative embodiments advantageously enable precise control of fluid delivery rates through IV tubing 270 without the roller clamp 32 (e.g., because of the controller 400 in conjunction with the check valves 232). Thus, illustrative embodiments enable fluid flow control without the roller clamp 32. Additionally, the slide clamp 30 is used to completely stop the IV from flowing, without having to adjust the roller clamp 32. This works by pinching the tubing 270 completely shut when sliding the tubing into the narrowest part of the clamp. Some embodiments may forego the slide clamp 30 and/or the roller clamp 32 because of the controller 400 and check valve 232 arrangement discussed below. Although not shown, the controller 400 (or a second controller 400) may also be pneumatically coupled with the drip chamber 227 of the secondary IV bag 22. In such an instance, the drip chamber 227 of the secondary IV bag 22 would also include the proximal check valve 232A and the distal check valve 232B.

In addition to manual IV setup, where the infusion of the IV depends upon pressure exerted by gravity and the rate is set manually by watching drops in the drip chamber and adjusting the roller clamp, illustrative embodiments may use pumps. It is more and more common for many IV setups in hospitals to be implemented using pumps that control the infusion rate on their own, only requiring the nurse to enter the infusion rate in mL/hr.

A variety of pumps may be used for precision fluid dispensing in medical settings. In medical applications, infusion pumps are useful for providing medicaments to patients, especially for the delivery of medical therapies requiring an extended period of time and through various routes of delivery, including intravenously, intra-arterially, subcutaneously, intradermally, intraperitoneally, in close proximity to nerves, and into an intraoperative site, epidural space or subarachnoid space.

While there are a variety of pumps for precise medical fluid delivery, syringe, peristaltic, and single and double-diagram designs tend to predominate both fields. Although each type has been successfully used, these pumps are subject to certain design and/or application challenges. Prior to the use of pumps, intravenous infusions were administered using gravity, a manually controlled resistance, and a visual indicator of the formation of drops into a visible chamber.

Peristaltic pumps include a flow cavity—a normally open fluid flow path, typically defined by a hollow length of flexible tubing, and a plurality of spaced apart "fingers" that sequentially deform the tubing. Regardless of whether the plurality of fingers are arranged in a linear, or more commonly a rotational arrangement, the sequential deformation of the tubing pressurizes the fluid within the flow cavity and propagates the fluid in a wave-like motion between the inlet and outlet ports of the pump, defined by the hollow length of tubing.

Like syringe pumps, even though peristaltic pumps have been successfully used, they are subject to certain design and/or application challenges. Because the fluid flow cavity is normally open, fluid can inadvertently continue to flow, even when the pump is not actuated. This can occur if the tubing leading from a source of fluid to the inlet port of the pump is not clamped. While this may be a nuisance in the laboratory, in clinical applications the results can be catastrophic. Also, the continuous compression of the tubing, defining the normally open flow path, can result in tube fatigue, which necessitates replacement of the tube. Tube replacements subsequently add to the operational cost of the system and introduce undesirable opportunities to disrupt the fluid flow path, which is often sterile or otherwise well controlled.

Peristaltic pumps also have challenges caused by the hydraulic head height, the position of the source of fluid above the pump, which can result in further inaccuracies with the flow rate from the pump. Additionally, peristaltic pumps are typically complex in nature, due to the number of parts required, which is directly related to the cost and reliability of the pump.

Illustrative embodiments of the invention advantageously solve problems associated with some of these pumps. For example, some embodiments may have a pneumatic control system which utilizes the familiar and low-cost configuration of a routine gravity administration set. A modification of the components of the tubing set 24, coupled with a precision pneumatic feedback control system 400 for pressure, can serve to precisely monitor and control the fluid flow to the patient 500.

FIG. 2A schematically shows details of the drip chamber 227 of the tubing set 24 in accordance with illustrative embodiments of the invention. As described previously, the chamber 227 has the spike 210 (e.g., a vented spike 210 to allow fluid flow from a rigid container 290), the proximal check valve 232A, and the distal check valve 232B. Coupled between the proximal check valve 232A and the distal check valve 232B is a pneumatic port 124 (with an optional closing cap 126). The pneumatic port 124 is coupled with controller 400 via the pneumatic tubing 26. An electromechanical valve 440 (also referred to as the pneumatic valve 440) selectively couples and uncouples the chamber 227 with the controller 400. As used in this application, the port 124 may be considered to be "between" the check valves 232A and 232B so long as the port 124 is pneumatically coupled with the volume formed between the sealed check valves 232 (i.e., when the check valves are closed). Thus, even if part of the port 124 overlaps with some portion of the check valve 232 (e.g., as in FIG. 2B), the port 124 is still be considered to be "between" the check valves 232. This may also be referred to as "pneumatically between".

When the check valves 232 are closed, and the electromechanical valve is closed (i.e., the reference volume 450 and the chamber 227 are pneumatically isolated), a working volume is defined within the chamber 227 (e.g., bounded by the walls of the chamber 227, and the boundary of the check valves 232 and the pneumatic valve 440). In general, this working volume may be known because the various parts of the system 100 are manufactured in accordance with a given specification. However, in some embodiments, the working volume may not be known.

The working volume has two portions: (1) a gas volume 38, and (2) a liquid volume 40. The interface 41 of the gas volume 38 and the liquid volume 40 is shown in dashed lines in FIG. 3. As liquid enters the chamber 227 through proximal check valve 232A, the liquid volume 40 increases (assuming liquid is not flowing out of the chamber 227). As liquid exits the chamber 227 through distal check valve 232B, the liquid volume 40 generally decreases (assuming liquid is not flowing into the chamber 227). A pressure sensor 462 measures the pressure of the gas volume 38. Although the pressure sensor 462 is shown as attached to the chamber 227, one of skill in the art understands that the pressure sensor 462 may occupy a variety of positions and may be pneumatically coupled with the gas volume 38.

Under automated pressure regulation by the controller 400, a certain level of negative differential pressure established in the chamber 227 moves liquid from the container 290 to travel through the spike 210 and into the chamber 227. The distal check valve 232B prevents retrograde flow from the patient 500. Pulling liquid into the chamber 227 using the negative pressure of the controller 400 defines a filling phase.

Under automated pressure regulation by the controller 400, a certain level of positive differential pressure established in the chamber 227 moves liquid from the chamber 227 towards the patient 500. The proximal check valve 232A prevents flow to the container 290. Moving liquid out of the chamber 227 towards the patient 500 defines a delivery phase. During the delivery phase, the hydrostatic pressure of the container 290 is blocked by the isolating action of the proximal check valve 232A, significantly mitigating (or making inconsequential) the effect of changing head heights of the container 290 on flow rates.

Figure 3:
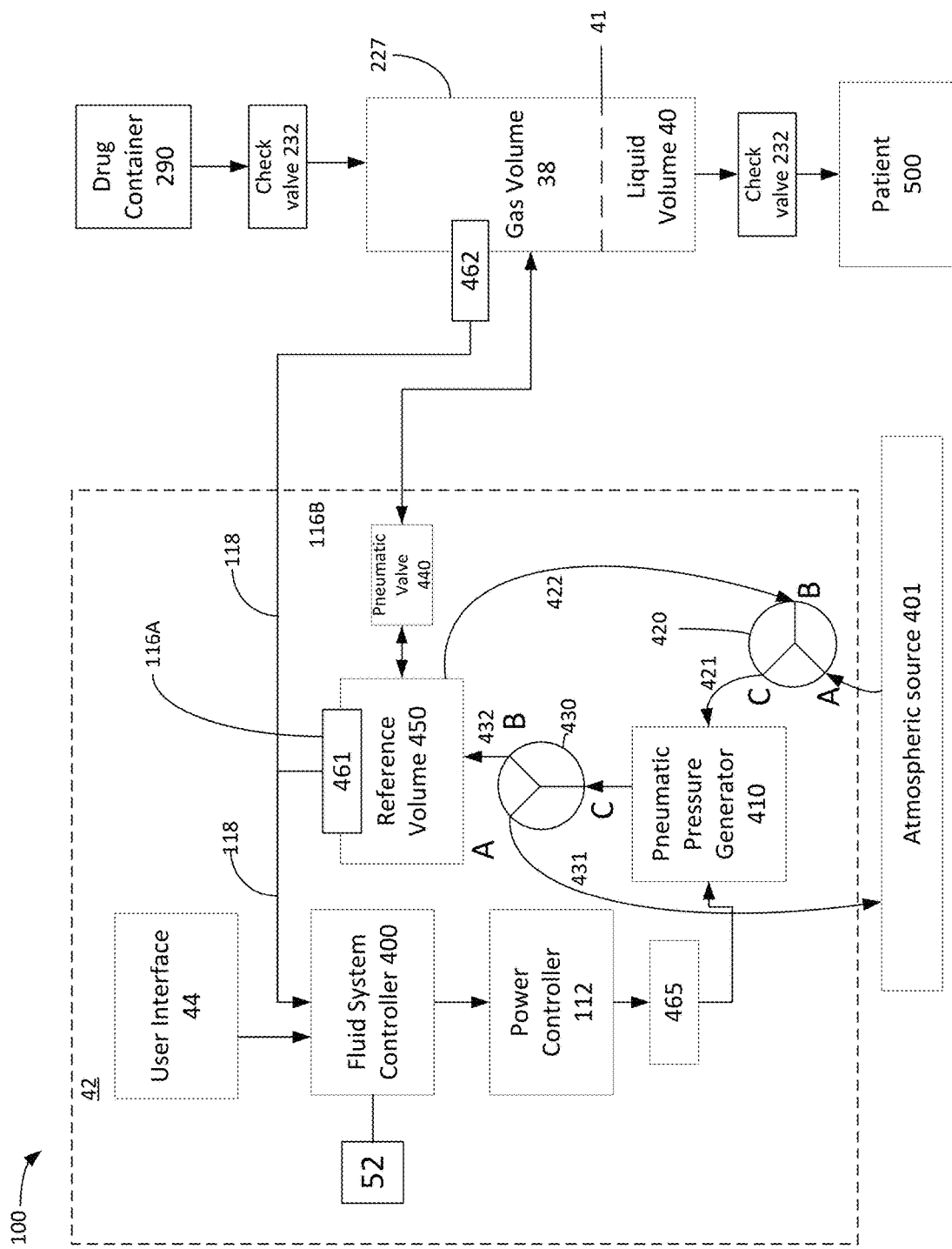
FIG. 3 schematically shows a detailed block diagram of the system in accordance with illustrative embodiments of the invention.

FIG. 3 schematically shows a detailed block diagram of the system 100 in accordance with illustrative embodiments of the invention. In particular, communications between the controller 400 and the drip chamber 227 are shown.

The controller 400 actuates the pneumatic pressure generator 410, receives pressure signals from the reference volume 450 and from the drip chamber 227. Those functions can be executed by separate components/modules, or share components/modules.

The pneumatic pressure generator 410 provides a precise flow and pressure profile in accordance with the settings of the controller 400. The controller 400 includes at least one microprocessor that can generate a selected power level to actuate the pressure generator 410, causing air to flow through the assembly. The input diverter valve 420 selectively pneumatically couples the pneumatic pressure generator 410 to an atmospheric source 401 or to the reference volume 450. Output diverter valve 430 connects generator 410 to the atmospheric source 401 or to the reference volume 450. The action of the valves 420 and 430 is controllable by the controller 400.

The system 100 enables selective operation of the drip chamber 227. Specifically, to pump fluid towards the patient 500, the system 100 must overcome the cracking pressure of distal check valve 232B. Accordingly, the system 100 generates a positive pressure in the drip chamber 227. When positive pressure is generated the drip chamber 227, fluid cannot flow upwardly towards the drug container 290 because of proximal check valve 232A. Thus, fluid flows towards the patient 500 through distal check valve 232B.

To increase pressure in the chamber 227, pneumatic valve 440 is opened, and gas is joined from the reference volume 450 to the drip chamber 227. To pump fluid from the reference volume 450, the input valve 420 is activated to pneumatically couple common branch C to selection A, allowing flow to come from the atmosphere 401 to the generator 410 via pneumatic connection 421. The output valve 430 is also activated to connect common branch C to selection B, allowing flow to come from the generator 410 to the reference volume 450 via pneumatic connection 432.

To refill the fluid in the drip chamber 227 from the drug container 290, the system 100 must overcome the cracking pressure of proximal check valve 232A. Accordingly, the system 100 generates a negative pressure in the drip chamber 227. When negative pressure is generated the drip chamber 227, fluid cannot flow upwardly from the patient 500 because of distal check valve 232B. Thus, fluid flows towards from the drug container 290 through proximal check valve 232A.

To decrease pressure in the drip chamber 227, the pneumatic valve 440 is opened, and fluid (e.g., gas) is pumped out of the drip chamber 227 towards the reference volume 450. To reduce pressure in the reference volume 450, the input valve 420 is activated to connect common branch C to selection B, allowing flow to come from the reference volume 450 to pressure generator 410 via pneumatic connection 422. The output valve 430 is activated to connect common branch C to selection A, allowing flow to come from the generator 410 to the atmospheric source 401 (e.g., ambient air) via pneumatic connection 431.

A reference pressure sensor 461 communicates with the reference volume 450 and sends a pressure signal 118 to the controller 400. Drip chamber pressure sensor 462 communicates with the drip chamber 227 and also sends a pressure signal 118 to the controller 400. The pressure signals 118 provide feedback that is used to control the flow rate of fluid inside the drip chamber 227.

The pneumatic valve 440 (e.g., an electromagnetic valve) selectively isolates the reference volume 450 from the drip chamber 227. When the pneumatic valve 440 is activated (e.g., by the controller 400) the reference volume 450 and the drip chamber 227 are pneumatically coupled. When the valve 440 is deactivated (e.g., de-energized), the reference volume 450 and the drip chamber 227 are pneumatically uncoupled. Illustrative embodiments repeat the selective pneumatic coupling and uncoupling of the known and unknown volume chambers, 450 and 227, respectively.

The controller 400 and/or the pneumatic pressure generator 410 are powered by an energy supply 465, which may be a battery or other known voltage and energy source. The user communicates with the controller 400 via the user interface 44, which may be a touchscreen interface 44 with both audio and visual feedback. In various embodiments, the housing 42 may include an inertial sensor 52 (e.g., an accelerometer and/or gyroscope) to provide information about the orientation of the controller 400 and/or the tubing set 24. In preferred embodiments, the drip chamber 227 is physically coupled with the housing 42. For example, the drip chamber 227 may be physically coupled with the housing 42 (e.g., the drip chamber 227 may fit within a chamber receiving portion 50 of the housing 42, see FIG. 2). Accordingly, the housing 42 and the chamber 227 may move and/or rotate together.

Figure 4:
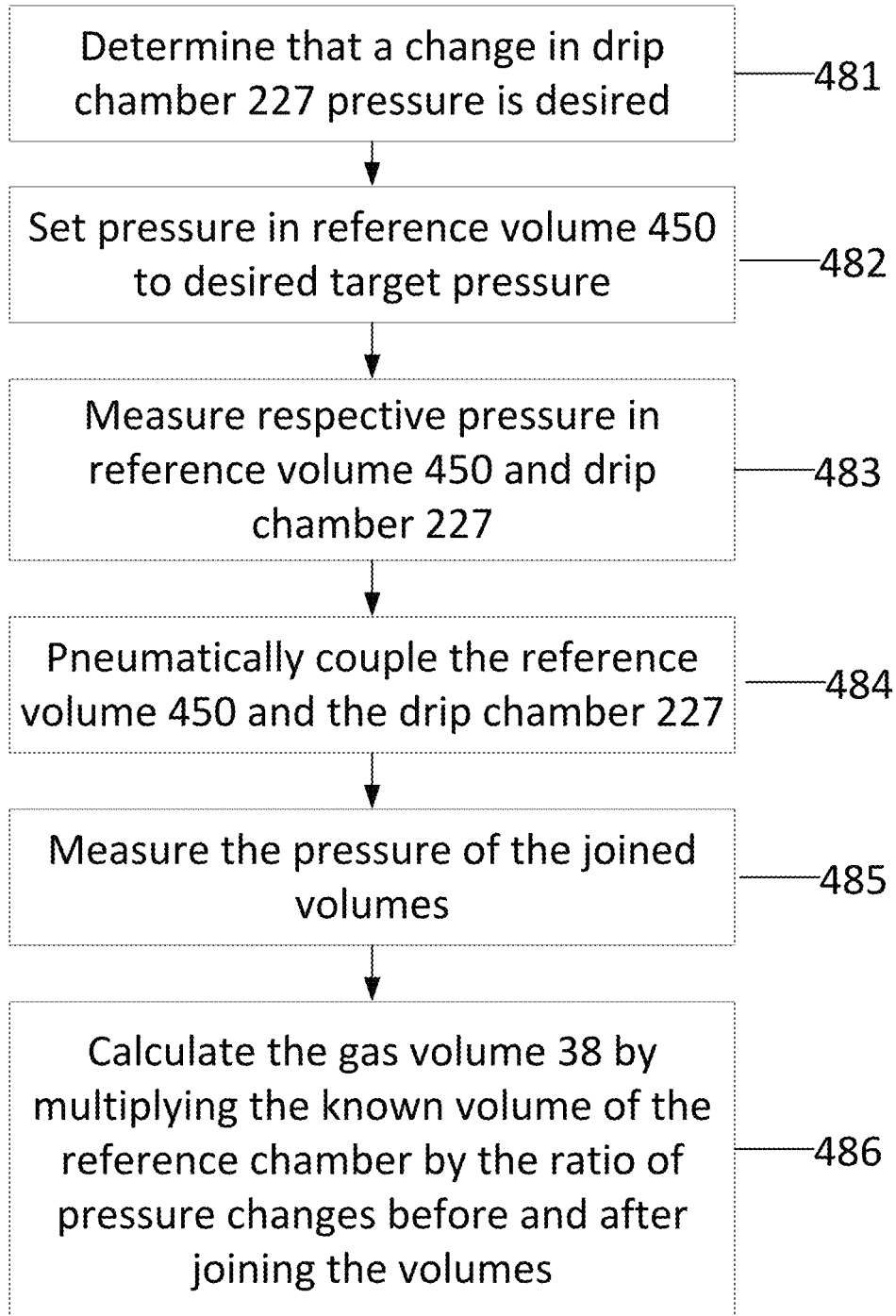
FIG. 4 schematically shows a process for computing gas volumes in accordance with illustrative embodiments of the invention.

FIG. 4 shows a process of computing the gas volume 38 in the drip chamber 227, which is variable and unknown. It should be noted that this process may be considered to be simplified from a longer process. Accordingly, the process may have other steps that those skilled in the art likely would use. In addition, some of the steps may be performed in a different order than that shown, or at the same time. Those skilled in the art therefore can modify the process as appropriate. Moreover, as with other figures, many of the structures noted are but one of a wide variety of different structures that may be used. Those skilled in the art can select the appropriate structures depending upon the application and other constraints. Accordingly, discussion of specific structures is not intended to limit various embodiments.

The process begins at step 481, where it is determined that a change in the drip chamber 227 pressure is desired. A change in the drip chamber 227 pressure may be desired, for example, to alter flow fluid rate, to begin fluid flow, or to stop fluid flow (e.g., to or from the drug container 290 or the tubing 270).

For example, during a filling phase of the infusion cycle, the pressure of the gas volume 38 is set to a relatively low pressure to bring liquid into the chamber 227 (e.g., from drug container 290). During a delivery phase of the infusion cycle, the pressure of the gas volume 38 is set to a relatively high pressure to compel liquid out of chamber 227 (e.g., towards the patient 500). In either case, it is determined that a change in the pressure in the chamber 227 is desirable. This may also be used as an opportunity to measure the gas volume 38.

At step 482, the pressure in the reference volume 450 is set to a desired target pressure using feedback control with the pneumatic generator 410 and the pressure sensor 461. At this point, the pneumatic valve 440 is closed, meaning that the reference volume 450 is pneumatically isolated from the drip chamber 227. At step 483, the pressure in the drip chamber 227 and the pressure in the reference volume 450 are measured prior to opening the pneumatic valve 440. At step 484, the pneumatic valve 440 is opened, allowing the gas volume 38 and the reference volume 450 to be joined pneumatically. After the valve 440 is opened, the pressures in the gas volume 38 and the reference volume 450 become the same because they are joined pneumatically. At step 485, the single pressure value may be measured (e.g., using either of the pressure sensors 461 and/or 462).

At step 486 the gas volume 38 in the drip chamber 227 is calculated. The changes in pressures recorded for the gas volume 38 and reference volume 450 in steps 483 and 485 form a ratio that is multiplied by the known volume of the reference volume 450, to compute the gas volume 38. It should be noted that this process calculates the gas volume 38, as opposed to the entire volume of the drip chamber 227 (which includes liquid volume 40). Indeed, in illustrative embodiments, the liquid volume 40 may be unknown (unless the entire volume of the drip chamber 227 is already known, e.g., 1 mL or 1000 mL).

Figure 5:
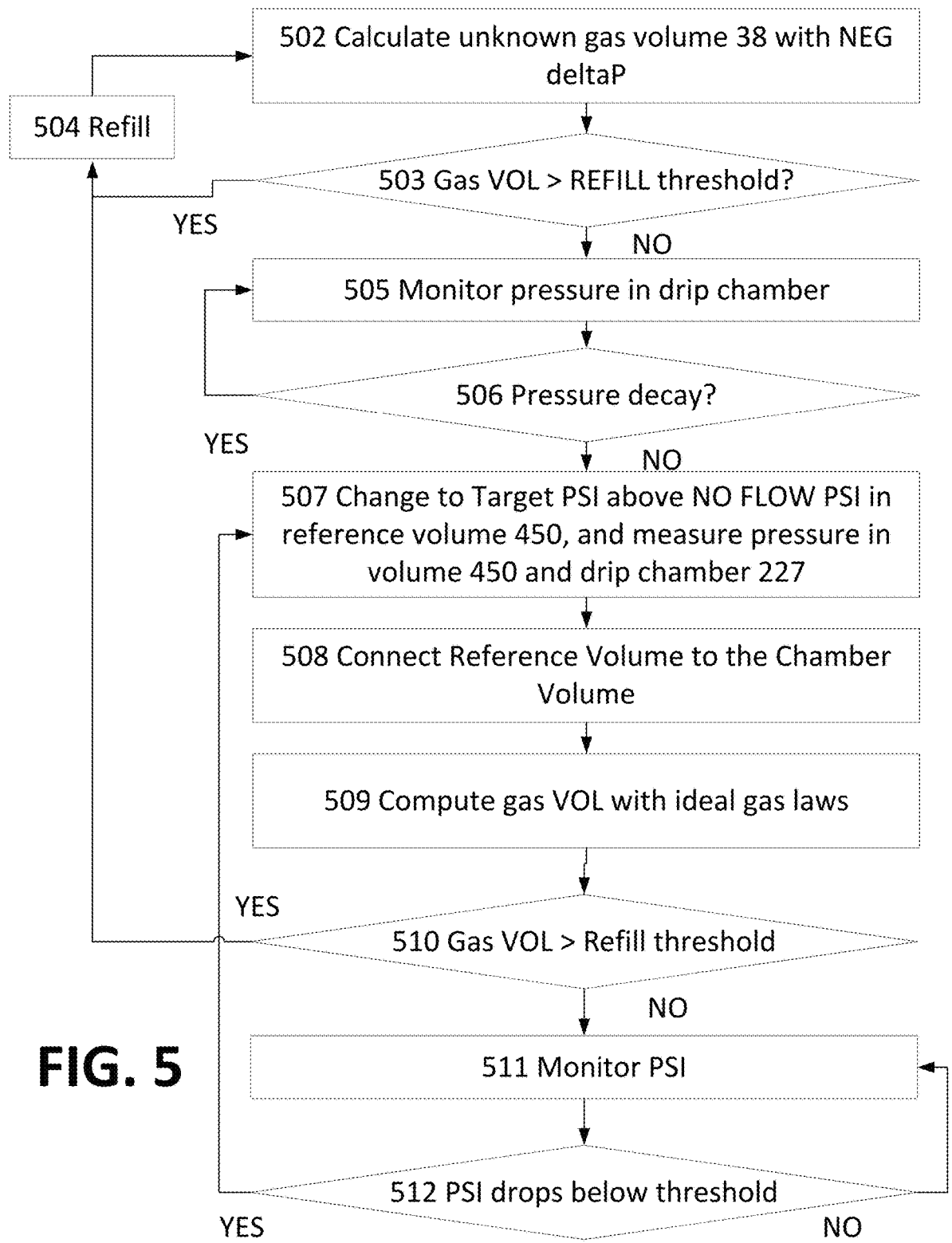
FIG. 5 shows a process of using the system to precisely deliver a drug to a patient in accordance with illustrative embodiments of the invention.

FIG. 5 shows a process of using the system 100 to precisely deliver a drug to a patient in accordance with illustrative embodiments of the invention. It should be noted that this process may be considered to be simplified from a longer process. Accordingly, the process may have other steps that those skilled in the art likely would use. In addition, some of the steps may be performed in a different order than that shown, or at the same time. Those skilled in the art therefore can modify the process as appropriate. Moreover, as with other figures, many of the structures noted are but one of a wide variety of different structures that may be used. Those skilled in the art can select the appropriate structures depending upon the application and other constraints. Accordingly, discussion of specific structures is not intended to limit various embodiments.

In illustrative embodiments, the process described in FIG. 5 achieves three objectives: (1) to ensure that the gas volume 38 stays between a range representing a nearly full drip chamber 227 and a nearly empty drip chamber 227; (2) to set the driving pressure in the drip chamber 227 to an adequate pressure level to achieve a targeted fluid flow; and (3) to create changes in drip chamber 227 pressure by joining the drip chamber 227 volume with a known reference volume 450, allowing the volume of the drip chamber 227 to be calculated.

The process begins at step 502, which calculates the gas volume 38 by actuating the pressure generator 410 to apply a negative pressure to the drip chamber 227. This process is described above with reference to FIG. 4. As described above, a series of valves may be activated to apply the negative pressure to the drip chamber 227. One of skill in the art knows how to calculate the gas volume 38, and details of this step are discussed in co-owned US patent publication US2020/0125124 entitled, "Airflow-Based Volumetric Pump," Ser. No. 16/656,449, filed Oct. 17, 2019 (the "'449 Application"), the disclosure of which is incorporated herein, in its entirety, by reference.

After the gas volume 38 is determined, step 503 asks whether the gas volume is greater than a refill threshold. If the gas volume 38 is greater than the refill threshold, then that means the liquid volume 40 has dropped to an undesirable rate. In various embodiments, the drip chamber 227 is preferably maintained with a liquid volume 40 in a range of between about 25% and about 75% of its capacity. If the gas volume 38 of the drip chamber 227 is greater than the refill threshold, then the process proceeds to step 504, which refills the drip chamber 227 with liquid by applying a controlled negative pressure to overcome the cracking pressure of the proximal check valve 232A and moving liquid from the container 290 into the chamber 227.

If the gas volume is not greater than the threshold, the process proceeds to step 505, which monitors the pressure in the drip chamber 227. During this step, the gas volume 38 may be isolated from the reference volume 450. Step 505 provides for the measurement of pressure to determine if fluid flow is occurring from the drip chamber 227 to the patient 500.

Step 506 analyzes the pressure signal captured in step 505 to detect a point where the pressure is no longer changing, representing a "no flow" condition. If there is pressure decay, the process continues. However, if there is no pressure decay, then that means the volume in the drip chamber 227 is constant, and therefore there is no fluid flow into or out of the drip chamber 227. Accordingly, this pressure may be preferred to as a "no flow PSI". It should be understood that no flow doesn't necessarily mean that the drip chamber 227 doesn't have any liquid. For example, the no-flow condition may be present because the pressure in the chamber 227 is not sufficient to overcome the distal check valve 232B cracking pressure, because of patient movement, increased resistance in the line, etc.), In some embodiments, the threshold for step 506 may be set to a certain pressure decay threshold (e.g., approach zero), not necessarily zero.

If there is an undesirable drop in flow, the process proceeds to step 507, which changes a target PSI in the reference volume 450 to above the no flow PSI. The reference volume 450 is filled to the target pressure in step 507 (e.g., while pneumatically isolated from the drip chamber 227). After filling, the pressure in the reference volume 450 and the drip chamber 227 are measured (while the two volumes are isolated by valve 440).

The process then proceeds to step 508, which pneumatically couples the reference volume 450 with the drip chamber 227 via opening of the valve 440. Pressure readings before and after the connection are captured via the pressure sensors 461 and 462. At step 509, a volume calculation is performed using the ideal gas laws and the measured pressures before and after coupling.

At step 510, if the gas volume is above the refill threshold, the process proceeds to step 504 which refills the drip chamber 227. However, if the remaining gas volume 38 is below a threshold, then the process proceeds to step 511, whichh monitors the pressure within the drip chamber 227. However, at step 512, if the pressure falls below the threshold, then the reference volume 450 is re-pressurized in step 507. The process then repeats steps 508-511. After a desired amount of fluid or medication has been delivered to the patient 500, the process comes to an end.

Figure 6:
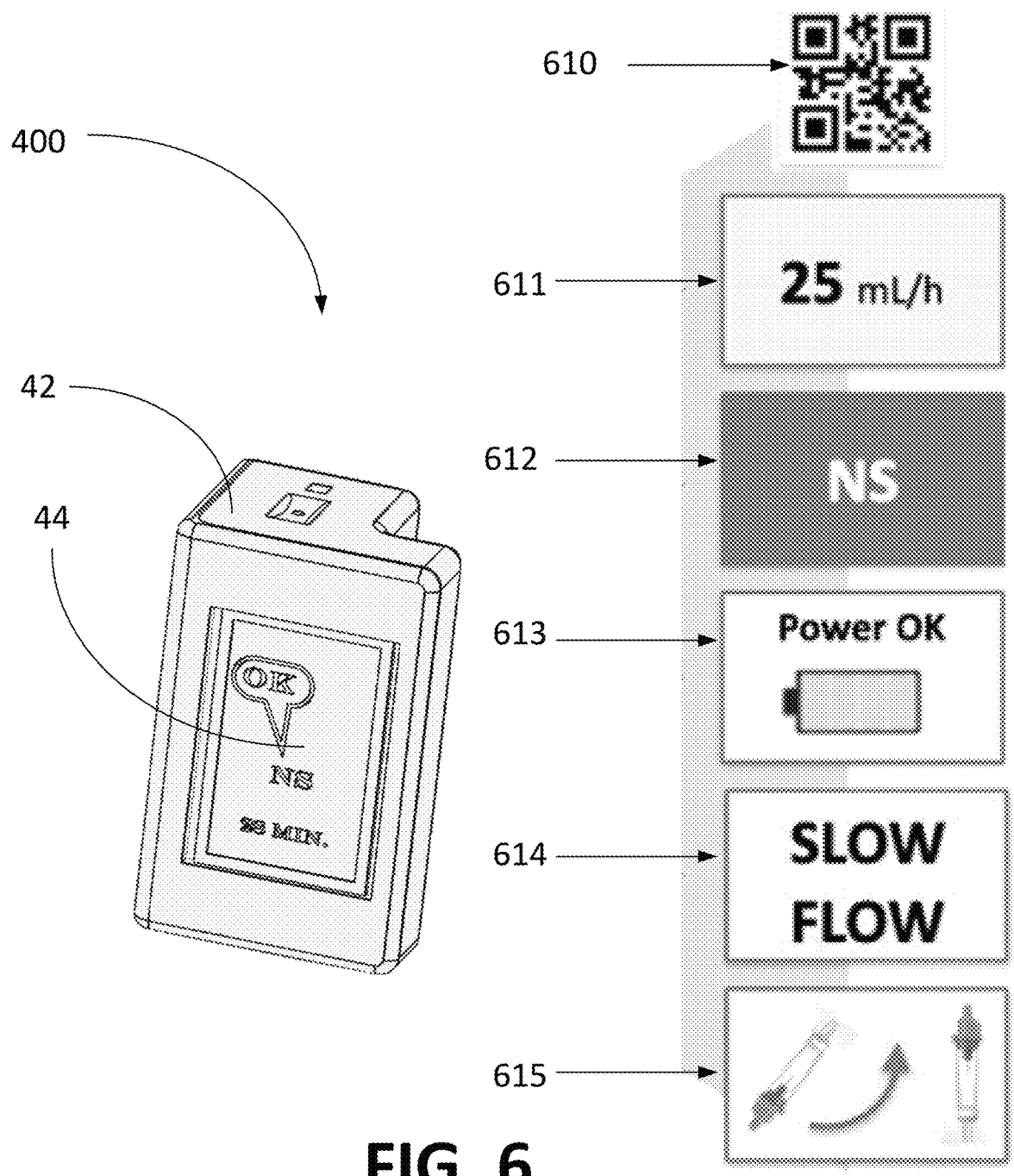
FIG. 6 schematically shows the user interface of the controller in accordance with illustrative embodiments of the invention.

FIG. 6 schematically shows the user interface 44 of the controller 400 in accordance with illustrative embodiments of the invention. The controller 400 offers a touchscreen interface 44 to communicate with the user. Accordingly, the user interface 44 may include a display. Among other things, the display may show an example QR code 610 that can be generated by the controller 400. This code can be used to securely link to a camera equipped mobile device, providing both a wireless address and a randomly generated key code. Additionally, or alternatively, the QR code 610 can communicate results of the infusion or other information to a mobile platform.

Among other things, the user interface 44 may display the active flow rate 611, the name of the drugs being delivered 612, remaining battery capacity 613, an alarm condition 614 (e.g., "Slow Flow"), and/or user prompts 615 (e.g., "restore system to upright position"). Alarms and alerts may be accompanied by audio alerts, as desired. Additionally, video displays can be shown.

Displays 610 to 615 are merely examples of information display and not meant to constrain or describe the full range of information to be displayed graphically. In some embodiments, the display may or may not be a touchscreen.

Figure 7:
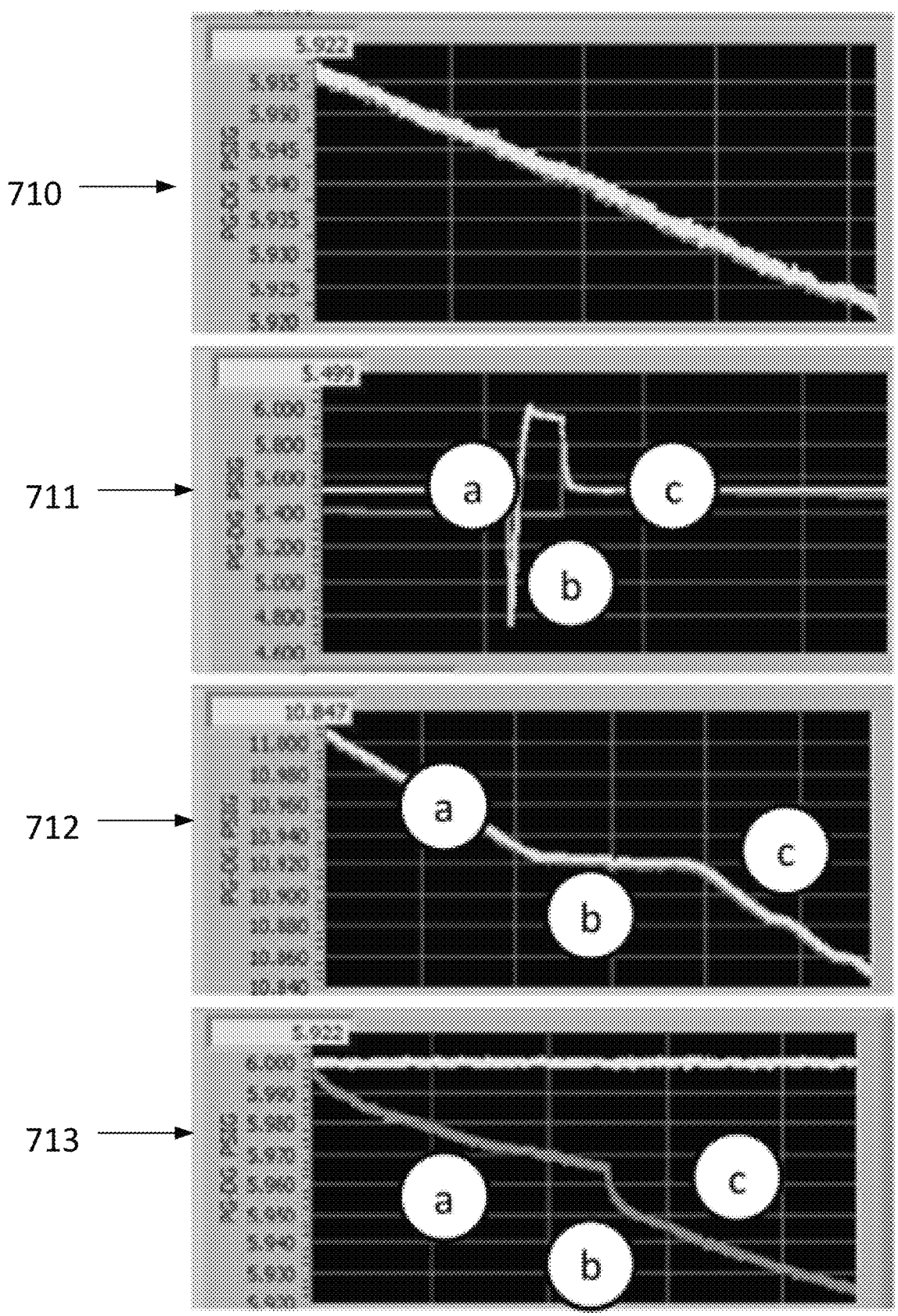
FIG. 7 shows sample pressure waveforms that can be used for automatic feedback control of the system in accordance with illustrative embodiments of the invention.

FIG. 7 shows sample pressure waveforms that can be used for feedback control, as more fully described in the '449 Application.

Waveform 710 illustrates an exemplary steady decay of pressure from the drip chamber 227, as measured by the pressure sensor 462. Knowing the volume of the drip chamber 227 and knowing the pressure of the atmospheric pressure 401 as measured, the slope of the waveform 710 is a direct indicator of the flow rate. Flow rate can be measured at a relatively high rate of several times per second, providing a way to watch for instantaneous flow rate changes.

Waveform 711 demonstrates the effects on pressure, as measured by the pressure sensors 461 and 462, when the valve 440 is activated to pneumatically couple the reference volume 450 with the drip chamber 227. Waveform 711 position "a" illustrates a slight decay in pressure as liquid leaves the drip chamber 227 towards the patient 500. At a point after "a", the pressure in the reference volume 450 is brought up to a target PSI. The dip in pressure after point "a" is a mechanical artifact of connecting the pressure generator 410 to the drip chamber 227. At point "b", the reference volume 450 is joined with the drip chamber 227 and the pressure has settled at point "c". By comparing the relative pressure changes, the unknown volume of the drip chamber 227 can be derived from the known volume of the reference volume 450.

Waveform 712 illustrates a response to an occluded output tube 270. At point "a", the pressure decay has a level of decay as a function of flow of liquid from the drip chamber 227. At point "b", the flow is occluded, and the response is seen as a diminished level of decay (e.g., "flat-lining" of pressure). At point "c", the release of the occlusion is seen as a resumption of the flow rate derived decay of pressure. In general, as liquid leaves the drip chamber 227, the liquid volume 40 is reduced, and the gas volume 38 is increased. As the gas volume 38 increases, the gas is less compressed, and therefore, pressure in the drip chamber 227 drops.

Waveform 713 illustrates a response to air traversing through output tube 270. At point "a", the pressure decay has a level of decay based on the flow of liquid from the chamber 227. At point "b", the reduced flow impedance of an air bubble is seen as an increased level of decay. At point "c", the resumption of liquid flow is seen as a restoration of the original flow rate derived decay of pressure. The large drop in pressure is caused by the large drop in resistance when the air bubble passes through output 270. After the air bubble is gone, the change of slope reverts to its normal pre-air bubble rate. The air bubble provides decreased resistance, decreased resistance results in increased flow, increased flow causes a rapid increase in the gas volume, and in turn represents a rapid decrease in pressure. The controller 400 may calculate how big the air bubble is. This calculation advantageously virtually eliminates unnecessary air bubble alarms for air bubbles that are not concerning.

Figure 8:
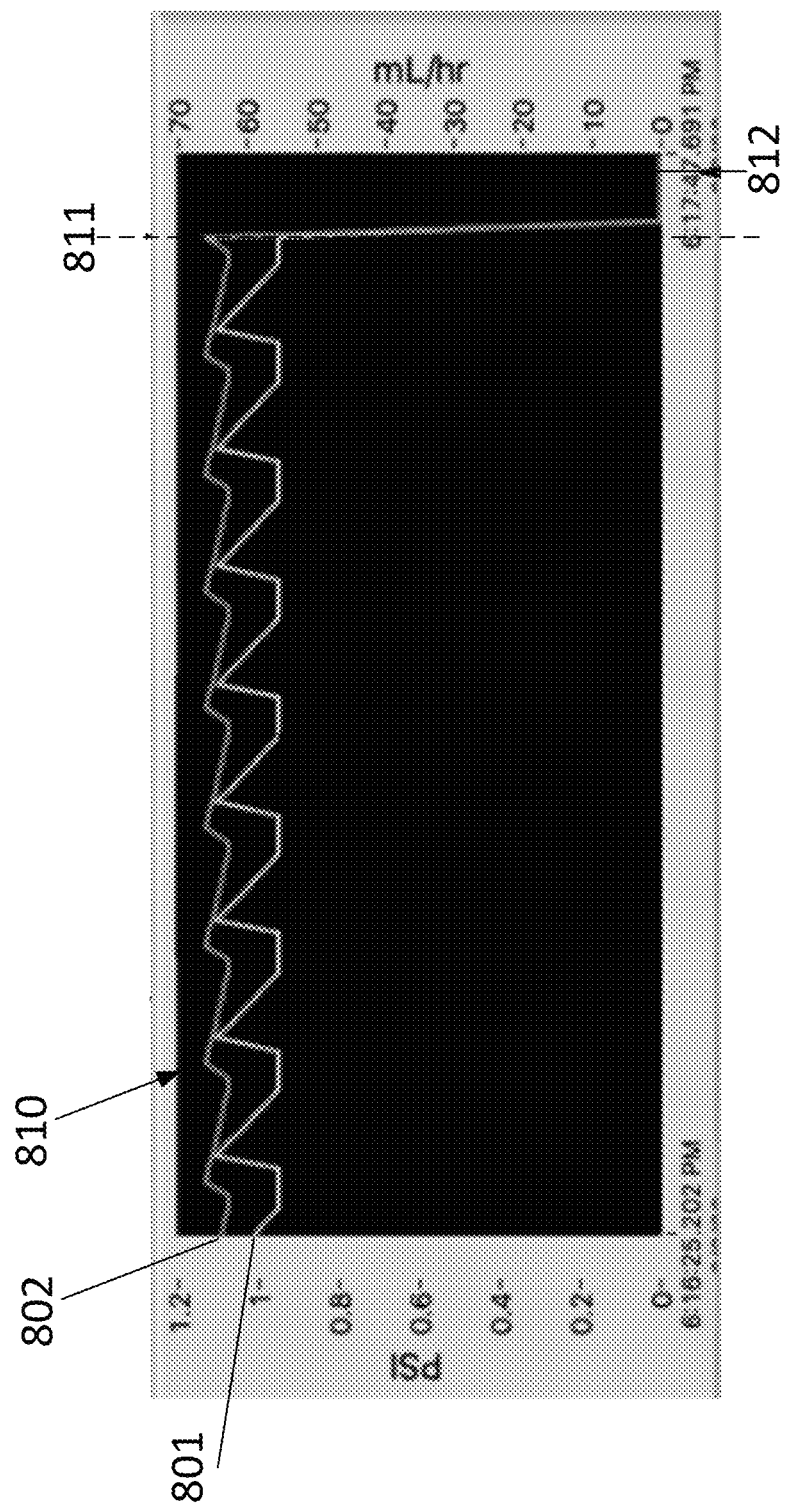
FIG. 8 shows sample waveforms displayed during a delivery phase in which the output line becomes occluded in accordance with illustrative embodiments of the invention.

FIG. 8 shows sample waveforms displayed during the delivery phase in which the output line becomes occluded. In one exemplary method of controlling flow rate, the driving pressure generated by the relevant pneumatic generator 410 is cycled as shown (e.g., pressure 801), resulting in a corresponding flow 802. The normal delivery is shown at delivery time 810 and the occlusion occurs at occlusion time 811, followed by post-occlusion time 812. The flow signal 802 (e.g., the first derivative of the pressure signal, doesn't require an actual flow rate sensor) responds to the occlusion and measures a rapid decrease in fluid flow. The controller 400 may, in response to flow 802, direct the output diverter valve 430 and the valve 440 to relieve the pressure 801 from the drip chamber 227 (e.g., by venting the drip chamber 227, resulting in zero gauge pressure in the chamber 227). Accordingly, in some embodiments, the pressure 801 advantageously does not increase in response to an occlusion, unlike conventional pumps.

Figure 9:
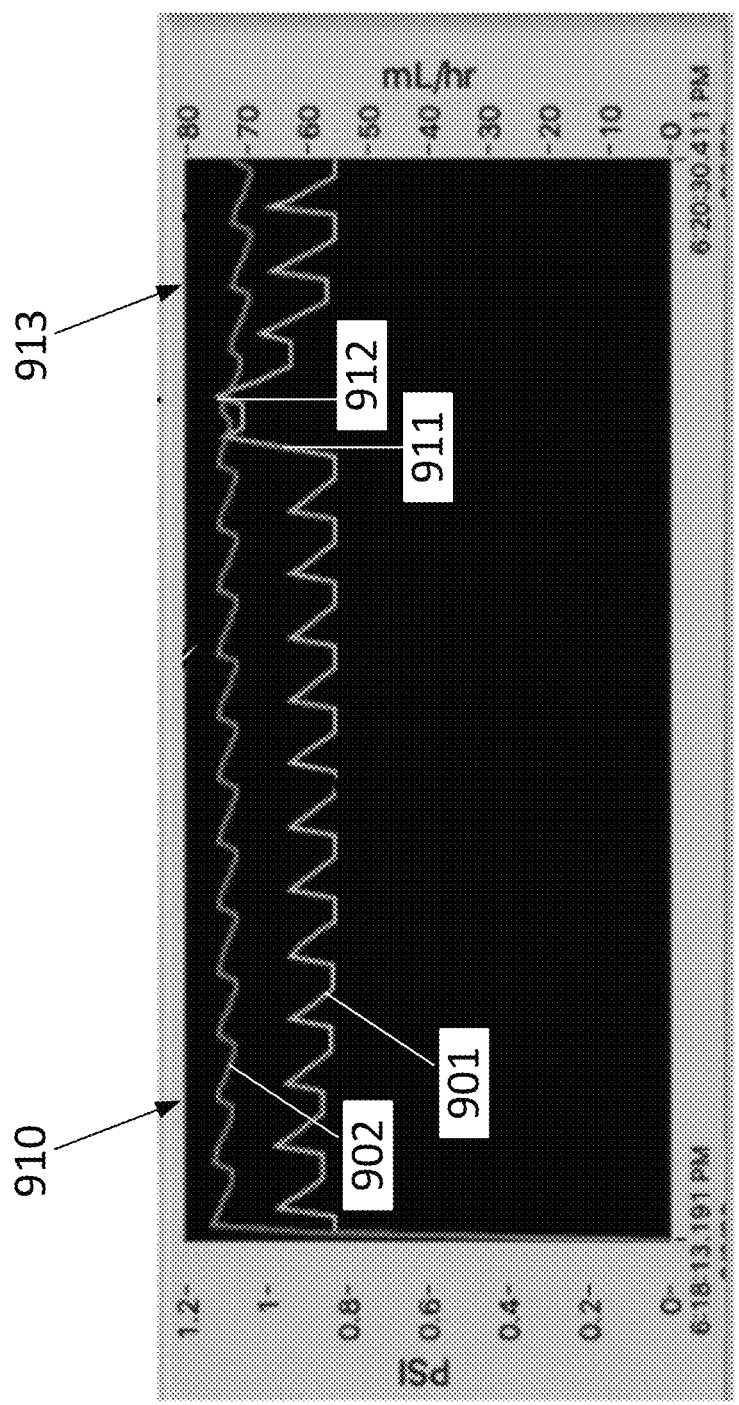
FIG. 9 shows sample waveforms displayed during a delivery phase in which the patient head height is changed in accordance with illustrative embodiments of the invention.

FIG. 9 shows sample waveforms displayed during the delivery phase in which the patient 500 head height is changed. The driving pressure generated by the pneumatic generator 410 is cycled as shown (e.g., as pressure 901), resulting in a corresponding flow 902. The normal delivery is shown at delivery time 910 and the position of the patient 500 or the bag 290 changes at position change time 911, followed by pressure response time 912 and then followed by a flow restored time 913. Flow signal 902 responds to the change in head height due to patient positional changes and measures a small decrease in fluid flow. The controller may, in response to changes in flow 902, increase the driving pressure until the flow rate has been restored to the target flow rate at Flow Restored Time 913. Additional details of this step are taught in the '449 Application.

FIG. 10 shows a table illustrating advantages of the above described illustrative embodiments as compared to common hazards for gravity based IV therapy. Hazard 301: Changes in head height create an unwanted change in flow rate if the relative position of the container 290 is changed. As described previously, IV infusion works because gravity pushes the fluid down through the IV tubing 270 into the patient's 500 vein. The higher the bag 290 is hung, the greater the gravitational pressure on the IV fluid to go downward through the tubing 270. If the IV bag 290 is not hung high enough, there will not be enough pressure caused by gravity to force the fluid into the vein. The IV bag 290 must be hung above the patient's 500 heart in order for there to be enough pressure for the IV fluid to infuse, and it is standard procedure to hang the IV bag 290 at least 3 feet above an adult patient's 500 heart to ensure there is enough pressure to keep the IV running at a constant rate.

Also, since changing the height of the IV bag 290 changes the gravitational pressure on the fluid, a change in the bag's height 290 over a patient's 500 heart changes the infusion rate of the IV. If the IV bag 290 gets higher above the patient's 500 heart, the IV infusion rate speeds up, and if the IV bag 290 gets lower to the patient's 500 heart, the IV infusion rate slows down. Because of this property, if the patient 500 was lying down when the IV was set up then sits up, the IV infusion rate slows down because the IV is now closer to the patient's 500 heart. In fact, technically any small movement by the patient or shift in position can change the rate at which the IV is infusing. Because of this, IVs are frequently checked to make sure that they are still infusing at the correct rate; usually once an hour and after any major position change of the patient.

Various embodiments advantageously adjust pressures automatically to accommodate changes in head height based on pressure feedback from the chamber 227.

Hazard 302: Pinched tube 270 commonly happens with a kink or occlusion of output tube 270. To that end, in various embodiments, a smaller bore tubing can be supported, because the drive pressure is not limited to head height pressure. If the bag 290 is 27 inches above the patient 500, the driving pressure using gravity is about 1 PSI. There is a low fluid path resistance. A smaller bore tube can offer a resistance to kinking and the controller 400 can detect an occluded line 270.

Hazard 303: Roller clamp 32 drift is a common problem with conventional IV gravity drips, in which the physical tubing 270 restriction drifts over time, causing unacceptable changes in flow. Illustrative embodiments eliminate or significantly mitigate the need for a roller clamp 32 altogether.

Hazard 304: Changes in patient 500 position is similar to Hazard 301 except that the differential pressure is changed by the change in the patient 500 position. Illustrative embodiments adjust the pressures automatically to fully accommodate changes in head height.

Hazard 305: Large Volume tubing 270 has an unwanted side effect of having a large contained volume of medication that remains in the tube 270. Illustrative embodiments allow for the use of a smaller bore tube 270, reducing the wasted contained volume.

Hazard 306: Changes in patient 500 site backpressure can unwantedly reduce flow. Conventional pumps often increase the pressure of delivery, causing other clinical problems. Illustrative embodiments monitor and detect changes in output impedance without significantly increasing the delivery pressure.

Hazard 307: Slide clamp 30 not released is a common lapse in procedure, preventing the start of an infusion. Illustrative embodiments do not require a slide clamp 30 because the sum of the opening pressures for check valves 232A and 232B which prevent undesired and uncontrolled flow. This undesired and uncontrolled flow, known as "free flow" is a major hazard in the field of infusion therapy.

Hazard 308: Tube disconnection can cause a free flow through tube 270 and may also suggest that the connection to the patient 500 is open, allowing bleeding and possible exsanguination. Various embodiments can detect the reduction in output impedance and possible changes in head height, creating an alarm condition where all fluid flow is stopped. A high urgency audio visual alarm can also direct attention to the possible open patient connection.

Hazard 309: Inversion of the drip chamber 227 may get air bubbles in the line. Inversion may cause air from the drip chamber 227 to enter output tube 270 and the patient 500, potentially causing harm from air embolism. Illustrative embodiments have a mechanical linkage or similar apparatus to the container 290 and tubing set 24, so that the controller 400 can use its accelerometer to detect an excessive angular tilt, creating an alarm condition in which flow is stopped and the user is requested to bring the system to an upright position whereupon flow can resume.

Hazard 310: Drip calculation error is a frequent occurrence whereupon the user is attempting to translate a drip interval into a fluid flow rate. Further confusion may occur when the prescription is specified in units of measure which require proper consideration of the drug concentration and patient weight. Often, the errors can be off by an order of magnitude, causing very serious flow administration errors. Illustrative embodiments can operate with a direct entry of flow rate in a single unit of measure, such as mL per hour.

No calculations are needed. Illustrative embodiments furthermore support wireless programming that can read the contents of the prescription directly from the visually encoded drug label (e.g., a barcode).

Hazard 311: Delays in infusion start are common and undocumented for gravity infusion. Various embodiments support wireless programming that can read the contents of the prescription directly from the encoded drug label, including the time of initiation. Deviations from the intended start time can deliver a warning and a notice in an audit trail for each infusion.

Hazard 312: Failure to log therapy in medical record can cascade into multiple errors, including the chance of duplicating the dose or failure to count the dose in the patient's fluid input/output balance. Illustrative embodiments support wireless reporting that can track the actual results from every infusion.

Figure 11:
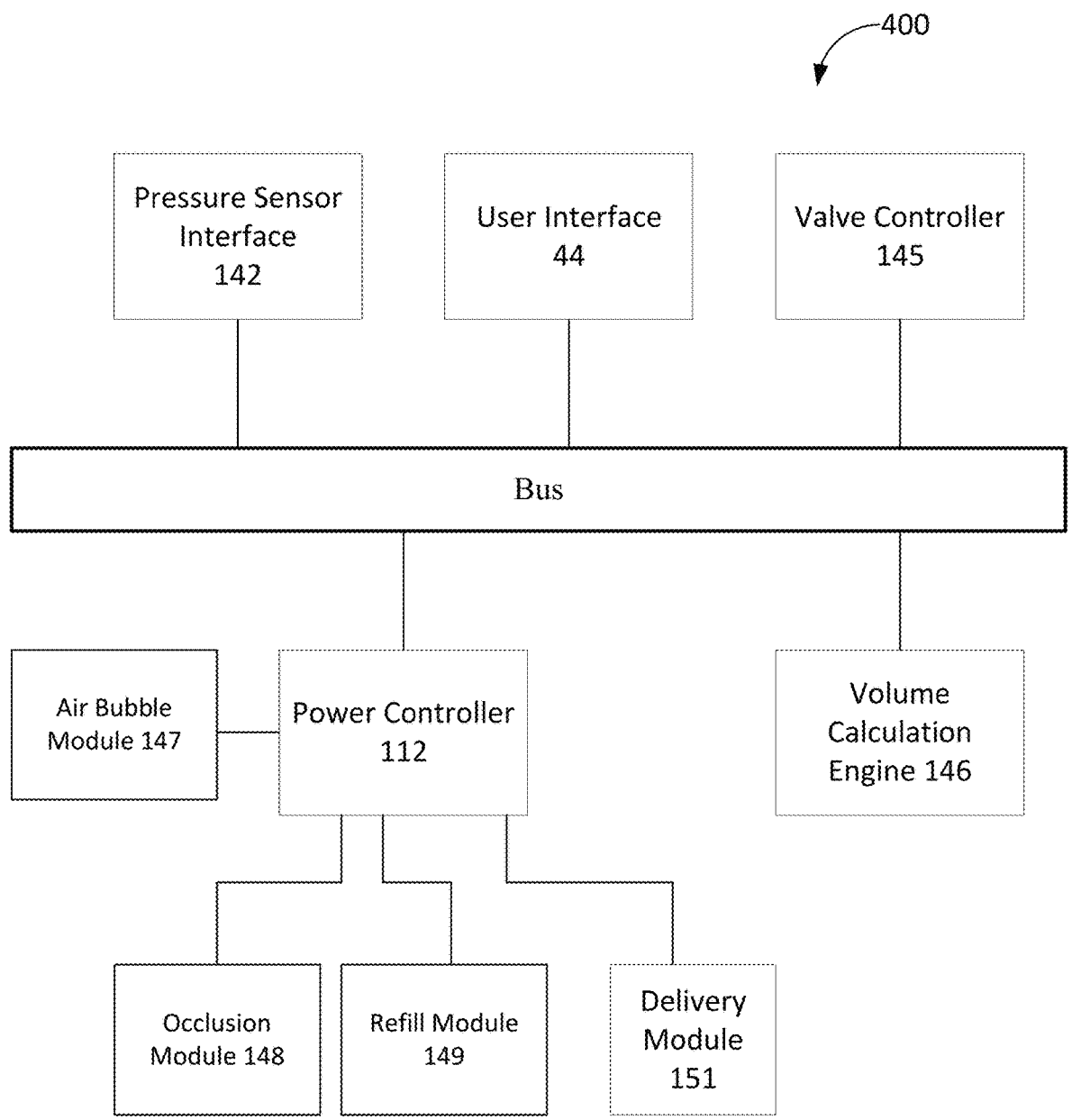
FIG. 11 schematically shows details of a fluid system controller in accordance with illustrative embodiments of the invention.

FIG. 11 schematically shows details of the fluid system controller 400 of FIG. 1 configured in accordance with illustrative embodiments of the invention. Each of these components is operatively connected by any conventional interconnect mechanism. FIG. 11 simply shows a bus communicating each of the components. Those skilled in the art should understand that this generalized representation can be modified to include other conventional direct or indirect connections. Accordingly, discussion of a bus is not intended to limit various embodiments.

Indeed, it should be noted that FIG. 11 only schematically shows each of these components. Those skilled in the art should understand that each of these components can be implemented in a variety of conventional manners, such as by using hardware, software, or a combination of hardware and software, across one or more other functional components. For example, a power controller 112 (discussed in detail below) may be implemented using a plurality of microprocessors executing firmware. As another example, the power controller 112 may be implemented using one or more application specific integrated circuits (i.e., "ASICs") and related software, or a combination of ASICs, discrete electronic components (e.g., integrated circuits), and microprocessors. Accordingly, the representation of the power controller 112 and other components in a single box of FIG. 11 is for simplicity purposes only. In fact, in some embodiments, the power controller of FIG. 11 is distributed across a plurality of different components—not necessarily within the same housing or chassis.

It should be reiterated that the representation of FIG. 11 is a significantly simplified representation of an actual fluid system controller 400. Those skilled in the art should understand that such a device has other physical and/or functional components, such as central processing units, other packet processing modules, and short-term memory. Accordingly, this discussion is not intended to suggest that FIG. 11 represents all of the elements of the fluid system controller 400. In fact, much of what was said here with regard to FIG. 11 can also be applied to components of the system 100 of FIG. 1 and/or FIG. 3.

The power controller 112 controls the power input provided to the pressure generator 410. The pressure generator 410 may be a tightly load coupled pneumatic driver, such as a microblower 410. The fluid system controller 400 instructs the power controller 112 to provide a power input to the pressure generator 410. Accordingly, the power controller 112 controls the pressure of the output gas 104. To that end, the user interface 44 of the controller 400 is configured to receive an input from the user. For example, the user interface 44 may receive a setting of a constant pressure or a constant flow rate that the pressure generator 410 should output. In various embodiments, the user interface 44 may be provided as a touchscreen display, a mechanical interface, and/or as a smartphone connected application.

The fluid system controller 400 also has a pressure sensor interface 142 configured to receive pressure signals 118 from the noted pressure sensors 461 and 462 (and/or other pressure sensors). As described previously with reference to FIG. 4, the pressure signals 118 provide a feedback loop to the fluid system controller 400 that allows the power controller 112 to adjust the power input provided to the pressure generator 410 as a function of the amount of pressure in one or both the reference volume 450 and the gas volume 38. Those skilled in the art will recognize that the feedback control loop can be substantially modified by, for example, adjusting coefficients for errors that are proportional, integrative, and derivative (PID). Such PID coefficients can even be modified during operation of the system 100, providing a wide dynamic range of behaviors.

The fluid system controller 400 also has a tightly load coupled (TLCP) power controller 112 configured to receive the settings from the user interface 44 (e.g., a constant pressure setting), receive pressure data from the pressure sensor interface 142, and to instruct the power controller 112 to increase or decrease pressure and/or flow rate. The power controller 112 performs calculations relating to what power input should be provided to the pressure generator 410 in accordance with the desired pressure setting in the reference volume 450 and/or the chamber 227. The controller 400 then provides that information to the power controller 112, which in turn provides the power input to the pressure generator 410.

The power controller 112 may have a number of functional modules that help provide automated feedback to the power controller. An occlusion module 148 detects an occlusion in the output tubing 270 caused by unexpected lack of decay in pressure (e.g., see waveform 712). The occlusion module 148 may, depending on the settings, instruct the power controller 112 to automatically stop powering the pressure generator 410. Alternatively, the occlusion module 148 may instruct the power controller 112 to automatically increase pressure in the drip chamber 227 to maintain a steady flow rate despite the occlusion. The occlusion module 148 may also communicate with the user interface 44 and provide a visible and/or audible warning.

In a similar manner, and air bubble module 147 may determine whether an air bubble has been output into tubing 270. This can be determined by a large rapid decrease in pressure as the air bubble leaves the drip chamber 227. For example, see waveform 713.

A refill module 149 may detect low liquid volume 40 and instruct the power controller 112 to take the necessary steps to refill the liquid volume 40 in the drip chamber 227. This process is described in additional detail in FIG. 5.

A delivery module 151 automatically controls delivery of fluid in accordance with a prescribed flow rate that may be received via the user interface 44. The delivery module 151 communicates with the power controller 112, which causes the pressure in the chamber 227, and the reference volume 450, to be sufficient to achieve the targeted flow rate and/or pressure. For example, a target flow rate of 30 mL/hr may be met using a chamber 227 pressure of 1.5 psi. Through successive volume calculations (as described in FIGS. 4 and 5) it may be determined that the flow rate is below the target flow rate. The delivery module 151 automatically adjusts the target driving pressure up to account for the change in flow rate (e.g., from 1.5 psi to 1.7 psi).

The fluid system controller 400 has a volume calculation engine 146 configured to calculate the unknown fluid volume in the drip chamber 227, based on the known volume in the reference volume 450, and the known pressures in the drip chamber 227 and the reference volume 450. In some embodiments, the fluid volume calculation engine 146 may also be configured to calculate the flow rate of fluid out of the drip chamber 227 Additionally, or alternatively, the volume calculation engine 146 may also be configured to measure fluid going into the drip chamber 227. Fluid flow directional references of gas or fluids should be considered to represent flow in either direction. The fluid system controller 400 also has a valve controller 145 that controls the opening and closing of the valve 440.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, programmable analog circuitry, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

Disclosed embodiments, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

The embodiments of the invention described above are intended to be merely exemplary; numerous variations and modifications will be apparent to those skilled in the art.

Such variations and modifications are intended to be within the scope of the present invention as defined by any of the appended claims.

What is claimed is:

1. A method of delivering a drug to a patient, the method comprising:
   providing a drip chamber, the drip chamber having:
      a proximal end coupled with a drug container and a distal end coupled with fluidic tubing that leads to a patient,
      the drip chamber including a proximal check valve, the proximal check valve configured to prevent fluid flow in a proximal direction, the proximal check valve further configured to allow fluid flow in a distal direction when a cracking pressure threshold of the proximal check valve is overcome,
      the drip chamber also including a distal check valve, the distal check valve configured to prevent fluid flow in the proximal direction, the distal check valve further configured to allow fluid flow in the distal direction when a cracking pressure threshold of the distal check valve is overcome, and
      a pneumatic port pneumatically coupled with a pneumatic generator, the pneumatic port being between the proximal check valve and the distal check valve;
   generating a negative pressure within the drip chamber using the pneumatic generator, the negative pressure sufficient to overcome the cracking pressure of the proximal check valve to move fluid from the drug container into the drip chamber.

2. The method as described by claim 1, further comprising:
   determining a volume of liquid in the drip chamber; and
   continuing to generate the negative pressure within the drip chamber until the volume of liquid in the drug container reaches a threshold; and
   ceasing the negative pressure sufficient to overcome the cracking pressure of the proximal check valve when the volume of liquid reaches the threshold.

3. The method as described by claim 1, further comprising:
   generating a positive pressure within the drip chamber using the pneumatic generator, the positive pressure sufficient to overcome the cracking pressure of the distal check valve to move fluid from the drip chamber into the tubing that leads to the patient.

4. The method as defined by claim 3, further comprising: adjusting the positive pressure within the chamber to achieve a given flow rate.

5. The method as defined by claim 3, further comprising: determining that there is an occlusion in the tubing that leads to the patient.

6. The method as defined by claim 5, further comprising: venting the drip chamber and/or providing an alert.

7. The method as defined by claim 3, further comprising; determining a volume of liquid in the drip chamber; and
   continuing to generate the positive pressure within the drip chamber until the volume of liquid in the drug container reaches a refill threshold; and
   ceasing the positive pressure sufficient to overcome the cracking pressure of the distal check valve when the volume of liquid reaches the refill threshold.

8. The method as defined by claim 7, further comprising: refilling the drip chamber when the volume of liquid reaches the refill threshold by generating a negative pressure in the drip chamber.

9. The method as described by claim 1, wherein the drip chamber is configured so that gas and liquid in the drip chamber are in direct contact.

10. The method as described by claim 1, wherein the pneumatic generator is a tightly load coupled pneumatic driver.

* * * * *